(12) United States Patent
Hamasaki et al.

(10) Patent No.: US 9,885,680 B2
(45) Date of Patent: Feb. 6, 2018

(54) ANALYSIS PACKAGE FOR DETECTING PARTICLES IN A SAMPLE LIQUID INCLUDING AN ANALYSIS CHIP MOUNTED ON A PACKAGE BOARD

(71) Applicant: KABUSHIKI KAISHA TOSHIBA, Minato-ku, Tokyo (JP)

(72) Inventors: Hiroshi Hamasaki, Hiratsuka Kanagawa (JP); Michihiko Nishigaki, Kawasaki Kanagawa (JP); Yutaka Onozuka, Yokohama Kanagawa (JP); Kentaro Kobayashi, Tokyo (JP); Hiroko Miki, Kawasaki Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 44 days.

(21) Appl. No.: 14/848,351

(22) Filed: Sep. 9, 2015

(65) Prior Publication Data
US 2016/0231265 A1    Aug. 11, 2016

(30) Foreign Application Priority Data
Feb. 9, 2015    (JP) .................................. 2015-023128

(51) Int. Cl.
*G01N 27/07*    (2006.01)
*B01L 3/00*    (2006.01)

(52) U.S. Cl.
CPC ............ *G01N 27/07* (2013.01); *B01L 3/5027* (2013.01); *B01L 2200/0647* (2013.01); *B01L 2300/0645* (2013.01); *B01L 2300/0681* (2013.01); *B01L 2300/0816* (2013.01); *B01L 2300/0887* (2013.01); *B01L 2400/0421* (2013.01); *B01L 2400/086* (2013.01)

(58) Field of Classification Search
CPC ........................... B01L 3/502715; G01N 27/00
USPC .................................................. 324/464–470
See application file for complete search history.

(56) References Cited

U.S. PATENT DOCUMENTS

| 2004/0144658 A1 | 7/2004 | Flory | |
|---|---|---|---|
| 2004/0248306 A1* | 12/2004 | Hernandez | B01L 3/5027 436/39 |
| 2006/0093517 A1* | 5/2006 | Yokoyama | B01L 3/502715 422/400 |

(Continued)

FOREIGN PATENT DOCUMENTS

| JP | 2014173935 A | 9/2014 |
|---|---|---|
| JP | 2016024013 A | 2/2016 |
| WO | 2016009674 A1 | 1/2016 |

*Primary Examiner* — Jeff Natalini
(74) *Attorney, Agent, or Firm* — Holtz, Holtz & Volek PC

(57) ABSTRACT

According to one embodiment, an analysis package including an analysis chip provided on a main surface of a semiconductor substrate, the chip including a flow channel, both ends of which are open at peripheral parts of the substrate, and a microaperture which is provided in a middle of the flow channel and which allows a particle to pass therethrough, a package board on which the chip is mounted, liquid receivers provided on the package board, the liquid receivers being connected to openings, and electrodes, at least parts of which are provided on parts of bottom surfaces of the liquid receivers, the electrodes being provided at positions corresponding to an upstream side and a downstream side of the microaperture.

14 Claims, 7 Drawing Sheets

(56) References Cited

U.S. PATENT DOCUMENTS

| | | | |
|---|---|---|---|
| 2008/0012583 A1* | 1/2008 | Audet | G06F 1/26 324/713 |
| 2008/0311375 A1 | 12/2008 | Harnack et al. | |
| 2014/0083859 A1* | 3/2014 | Baeumner | B81B 1/006 204/601 |
| 2014/0252505 A1* | 9/2014 | Kobayashi | G01N 15/0656 257/414 |
| 2014/0320849 A1* | 10/2014 | Chou | B03C 5/026 356/72 |

* cited by examiner

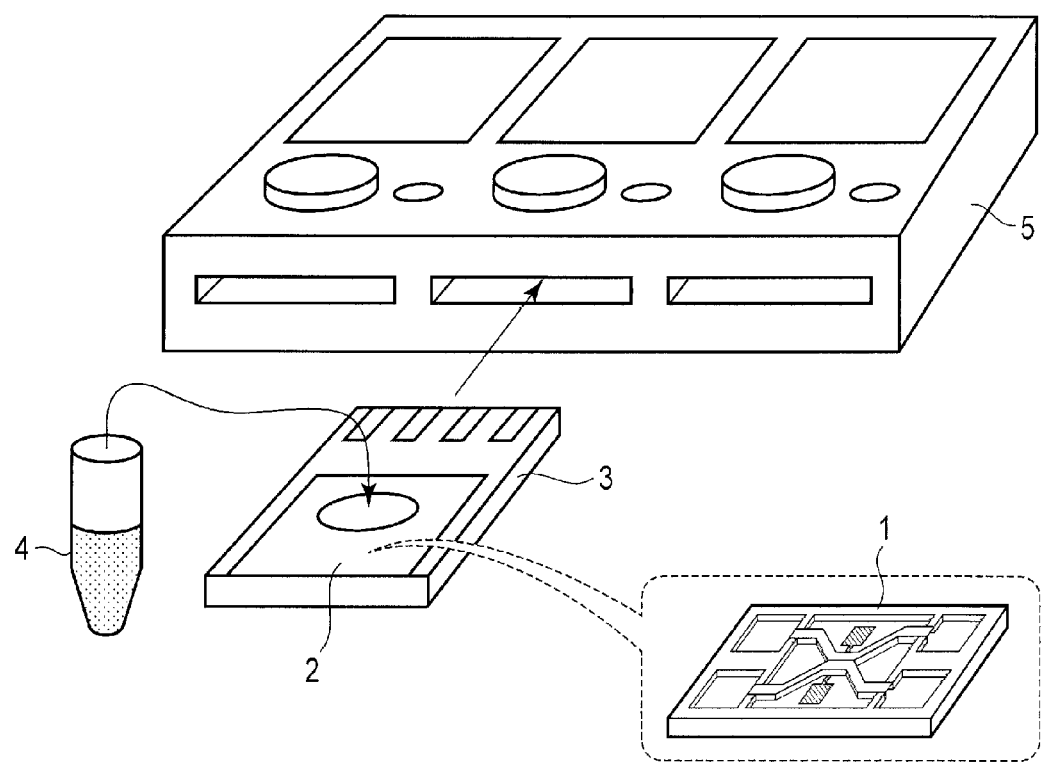
F I G. 1

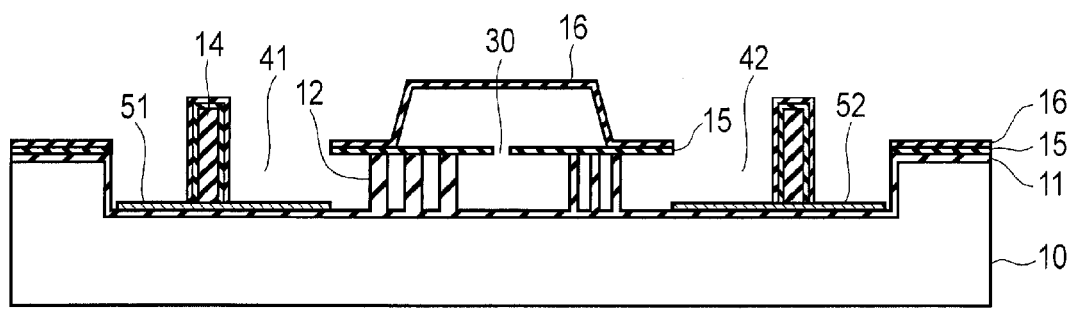
F I G. 3
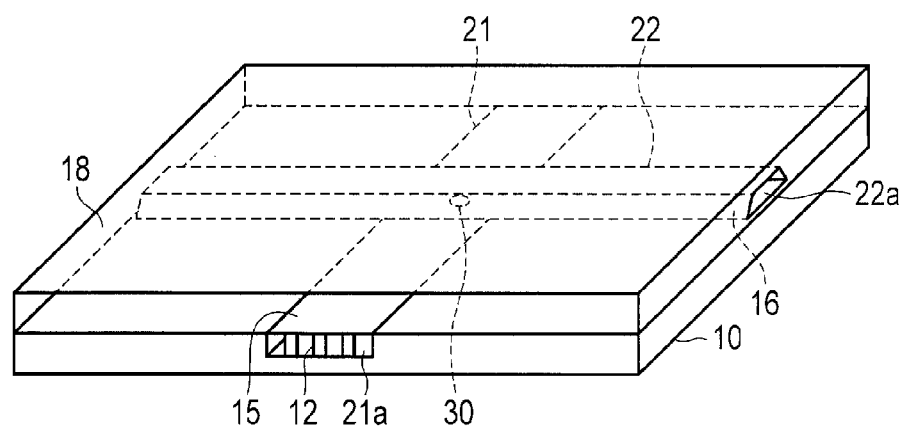
F I G. 4

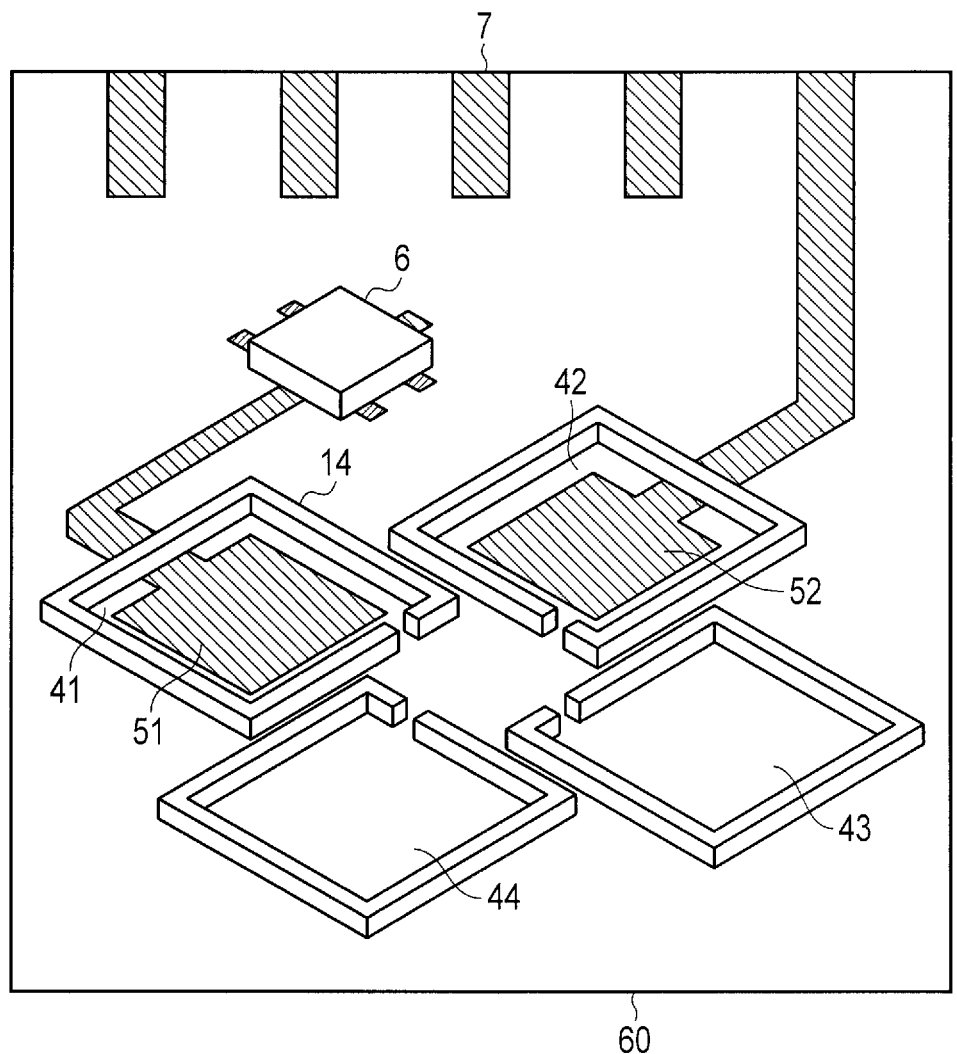
F I G. 5

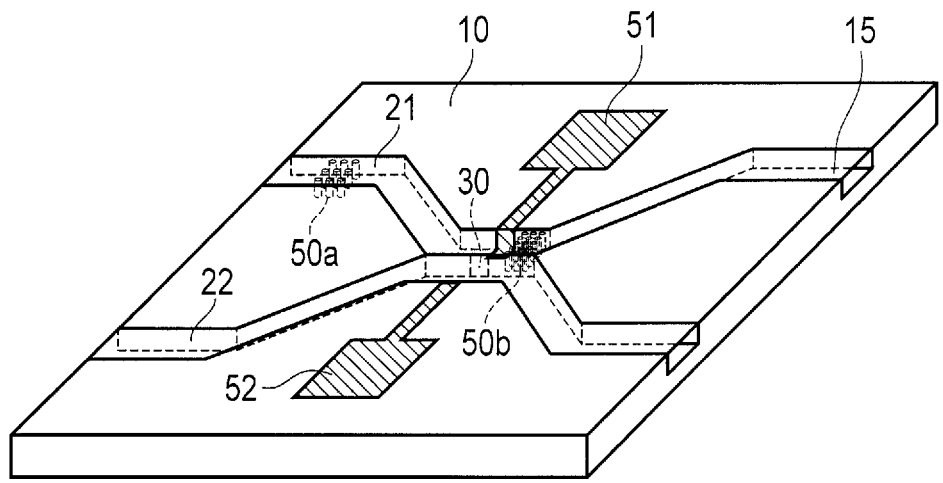
F I G. 10
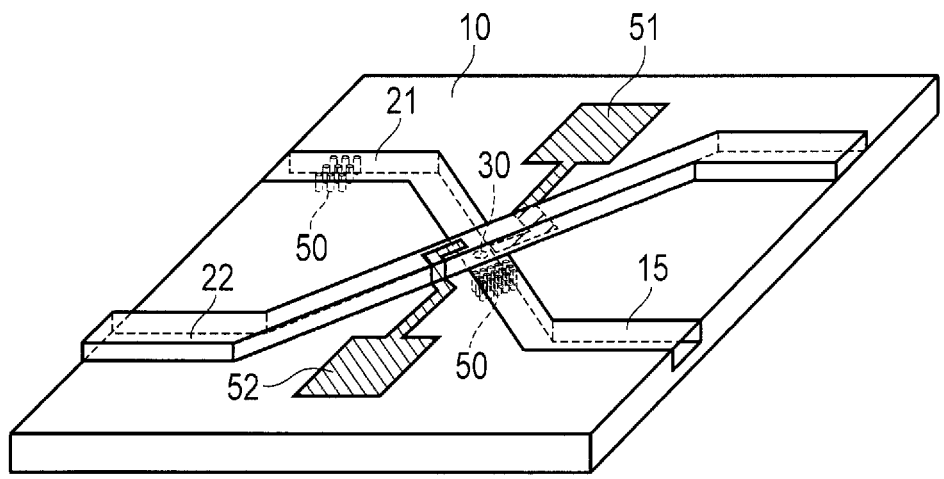
F I G. 11

US 9,885,680 B2

ANALYSIS PACKAGE FOR DETECTING PARTICLES IN A SAMPLE LIQUID INCLUDING AN ANALYSIS CHIP MOUNTED ON A PACKAGE BOARD

CROSS-REFERENCE TO RELATED APPLICATIONS

This application is based upon and claims the benefit of priority from Japanese Patent Application No. 2015-023128, filed Feb. 9, 2015, the entire contents of which are incorporated herein by reference.

FIELD

Embodiments described herein relate generally to an analysis package for detecting particles in a sample liquid, and further relate generally to an analysis chip and a package board.

BACKGROUND

In recent years, a semiconductor microanalysis chip on which microfluidic devices such as microflow channels and detection mechanisms are integrated has been attracting attention in the field of biotechnology and healthcare. In this kind of chip, particles and biopolymers included in a sample liquid can be detected by letting the sample liquid flow in a flow channel and acquiring the displacement of the particles, etc., in the sample liquid as an electrical signal by the variation of electrical resistance.

BRIEF DESCRIPTION OF THE DRAWINGS

FIG. 1 is a perspective view showing a structure example of a microanalysis system;

FIG. 3 is a cross-sectional view taken along line A-A' of FIG. 2;

FIG. 4 is a perspective view showing a structure of a semiconductor microanalysis chip used in a microanalysis package according to a first embodiment;

FIG. 5 is a perspective view showing a structure of a package board used in the microanalysis package according to the first embodiment;

FIG. 10 is a perspective view showing a modification of the semiconductor microanalysis chip used in the first and second embodiments; and FIG. 11 is a perspective view showing a modification of the semiconductor microanalysis chip used in the first and second embodiments.

DETAILED DESCRIPTION

Figure 2:
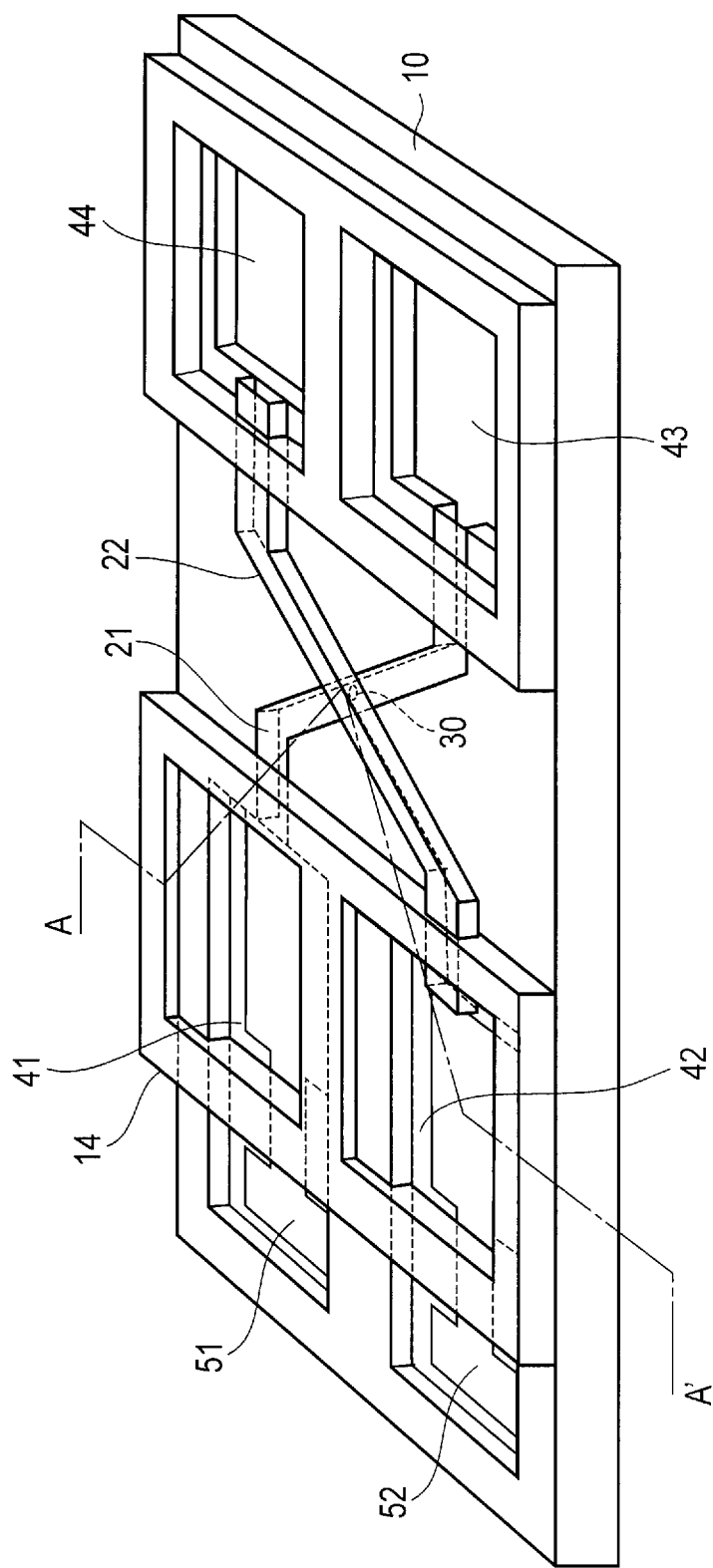
FIG. 2 is a perspective view showing a schematic structure of a semiconductor microanalysis chip used in the microanalysis system of FIG. 1.

In general, according to one embodiment, an analysis package comprises: an analysis chip provided on a main surface of a semiconductor substrate, the chip comprising a flow channel, both ends of which are open at peripheral parts of the semiconductor substrate, and a microaperture which is provided in a middle of the flow channel and which allows a particle to pass therethrough; a package board on which the analysis chip is mounted; liquid receivers provided on the package board, the liquid receivers being connected to openings of the flow channel of the semiconductor substrate, respectively; and electrodes, at least parts of which are provided on parts of bottom surfaces of the liquid receivers, the electrodes being provided at positions corresponding to an upstream side and a downstream side of the microaperture, respectively.

Analysis packages of embodiments, for instance, microanalysis packages will be described hereinafter with reference to the accompanying drawings.

(First Embodiment)

FIG. 1 is for explaining a first embodiment, and is a perspective view showing a structure example of a microanalysis system.

An analysis chip, for instance, a semiconductor microanalysis chip 1 does not function alone, and is mounted on a package board with a detection IC. Moreover, the semiconductor microanalysis chip 1 has weak strength, and thus is molded from a resin, etc., when being actually used as a product. A package formed by resin molding is a microanalysis package 2.

The microanalysis package 2 is generally set in a cassette 3 when being used. In addition, the microanalysis package 2 is provided for a test of particles by inserting the cassette 3 into a determination device 5 after dropping a sample liquid 4 onto a necessary portion of the chip 1.

FIG. 2 is a perspective view showing a basic structure of the semiconductor microanalysis chip. FIG. 3 is a cross-sectional view taken along line A-A' of FIG. 2.

The semiconductor microanalysis chip 1 is composed of a semiconductor substrate 10, first and second microflow channels 21 and 22, a microaperture 30 for particle detection, first to fourth reservoirs 41 to 44, and first and second electrodes 51 and 52 formed in the reservoirs 41 and 42. In addition, an insulating film 11 is formed on at least a main surface of the semiconductor substrate 10, and further, insulating films (cap layers) 15 and 16 which cover top surfaces of the microflow channels 21 and 22 are formed.

More specifically, a part of the main surface of the semiconductor substrate 10 is excavated to form the first microflow channel 21 of a substrate excavation type. Moreover, the second microflow channel 22 of an insulating film tunnel type forming a hollow structure of the insulating film 16 is formed on the semiconductor substrate 10 to intersect with the first microflow channel 21. The second microflow channel 22 is formed, not in the semiconductor substrate 10, but on the semiconductor substrate 10. Thus, the second microflow channel 22 is located above the first microflow channel 21. Furthermore, the second microflow channel 22 intersects with the first microflow channel 21 at a central portion of the semiconductor substrate 10, and the microaperture 30 for detection is formed at an intersection thereof.

In addition, to form the second microflow channel 22, a pattern of a sacrificial layer is formed in a line on the semiconductor substrate 10, and then, the insulating film 16 is formed to cover the sacrificial layer. Then, a flow channel of an insulating film tunnel type is formed by removing the sacrificial layer. In addition, micropillars 12 may be disposed in array in the flow channels 21 and 22. These pillars 12 can be formed simultaneously with substrate excavation for the formation of a microflow channel by providing circular masks on a surface of the semiconductor substrate 10. In addition, the pillars 12 accelerate the flow of a sample liquid by capillarity, and function as a filter. That is, the pillars 12 can also function as a filter for preventing a large particle from closing the detection hole 30 by making an interval between the pillars 12 slightly larger than a particle to be detected.

On one end side of the first microflow channel 21, a surrounding bank 14 is formed on the semiconductor substrate 10, whereby the first reservoir (liquid receiver) 41 is formed. It should be noted that the reservoir 41 may be formed by excavating a part of the semiconductor substrate 10 when forming the flow channel. One end of the first microflow channel 21 is connected to the reservoir 41. In addition, the first electrode 51 is formed on the surface of the semiconductor substrate 10 in the first reservoir 41. A part of the electrode 51 is introduced to the outside of the reservoir 41 through a bottom portion of the bank 14.

On one end side of the second microflow channel 22, a surrounding bank 14 is formed on the semiconductor substrate 10, whereby the second reservoir 42 is formed. The second reservoir 42 has substantially the same structure as that of the first reservoir 41, and is connected to the second microflow channel 22. In addition, the second electrode 52 is formed on the surface of the semiconductor substrate 10 in the second reservoir 42. A part of the electrode 52 is introduced to the outside of the reservoir 42 through a bottom portion of the bank 14.

On the other end side of the first microflow channel 21, a surrounding bank 14 is formed on the semiconductor substrate 10, whereby the third reservoir 43 is formed. The structure of the third reservoir 43 is the same as that of the first reservoir 41, except that the electrode 51 is not provided. On the other end side of the second microflow channel 22, a surrounding bank 14 is formed on the semiconductor substrate 10, whereby the fourth reservoir 44 is formed. The structure of the fourth reservoir 44 is the same as that of the reservoir 42, except that the electrode 52 is not provided.

As described above, the first microflow channel 21 connects the first reservoir 41 and the third reservoir 43, and the top surface thereof is covered by the cap layer 15. The second microflow channel 22 connects the second reservoir 42 and the fourth reservoir 44, and the top surface and side surfaces thereof are covered by the cap layer 16.

When a liquid such as a sample liquid is dropped into the first reservoir 41 of the semiconductor microanalysis chip like this, the dropped liquid spreads in the first reservoir 41, and is introduced into the first microflow channel 21. The liquid introduced into the first microflow channel 21 further reaches the third reservoir 43. Similarly, when a liquid such as a sample liquid is dropped into the second reservoir 42, the dropped liquid spreads in the second reservoir 42, and is introduced into the second microflow channel 22. The liquid introduced into the second microflow channel 22 further reaches the fourth reservoir 44.

At this time, the liquid in the first microflow channel 21 is electrically connected to the first electrode 51. Similarly, the liquid in the second microflow channel 22 is electrically connected to the second electrode 52. Moreover, the liquid in the first microflow channel 21 and the liquid in the second microflow channel 22 contact each other through the microaperture 30. Therefore, the first electrode 51 and the second electrode 52 are electrically connected through the dropped liquids.

When a voltage is applied between the first electrode 51 and the second electrode 52 in the state where an electrically conductive sample liquid including a specimen such as particles is dropped into the first reservoir 41 and the second reservoir 42, an ion current flows between the electrodes 51 and 52. That is, an ion current depending on the electrical conductivity of the sample liquid, the sizes and the qualities of materials of the first and second electrodes 51 and 52, the sizes of the first and second microflow channels 21 and 22, the size of the microaperture 30, etc., flows. In addition, an electric field according to the current density of an ion current is produced in the first and second microflow channels 21 and 22 and the microaperture 30, and the electric field intensity is the largest especially in the vicinity of the microaperture 30 which is smaller in size than the first and second microflow channels 21 and 22. Because a surface of a specimen such as particles in a sample liquid is generally electrified, electrophoresis occurs because of this surface charge and the above-described electric field.

In the vicinity of the microaperture 30 where the electric field intensity is high, the movement of particles due to electrophoresis increases, and in some cases, the particles may move from the first microflow channel 21 to the second microflow channel 22 through the microaperture 30, or move in reverse. At this time, because the particles remove a sample liquid in the microaperture 30, the electrical resistance of the microaperture 30 rises, and consequently, the size of an ion current decreases. The amount of change and a time of change in this ion current correspond to the size of a particle passing through the microaperture 30. Therefore, the size of a particle in a sample liquid can be electrically analyzed by measuring the size of an ion current flowing between the first electrode 51 and the second electrode 52.

It should be noted that if particles move from the first flow channel 21 to the second flow channel 22 through the microaperture 30 in one direction, a sample liquid need not be introduced into the second flow channel 22, and an electrolyte solution which enables electrical detection between the electrodes 51 and 52 may be introduced.

In the semiconductor microanalysis chip shown in FIG. 2 and FIG. 3, since the microflow channels 21 and 22 and the reservoirs 41 to 44 are formed on the semiconductor substrate 10, there has been a problem that the semiconductor substrate 10, which is expensive, is large, and the cost thereof is increased. Thus, in the present embodiment, only the flow channels are formed on the semiconductor substrate 10, and the reservoirs are formed on the package board on which the semiconductor microanalysis chip is mounted.

Figure 6:
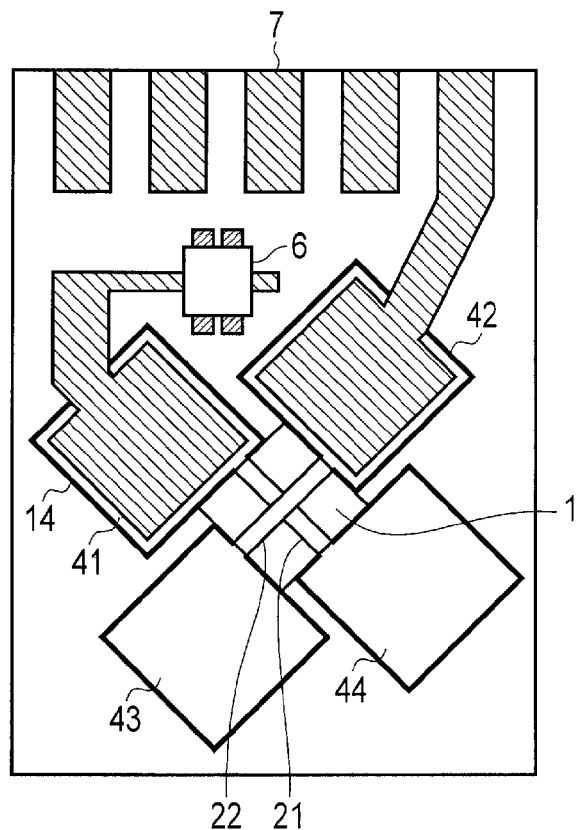
FIG. 6 is a plan view showing a schematic structure of the microanalysis package according to the first embodiment.

FIG. 4 to FIG. 6 are illustrations for explaining a schematic structure of a microanalysis package according to the first embodiment. FIG. 4 is a perspective view showing a semiconductor microanalysis chip alone. FIG. 5 is a perspective view showing a structure of a package board. FIG. 6 is a plan view showing the state where the semiconductor microanalysis chip is mounted on the package board.

As shown in FIG. 4, a first microflow channel 21 of a substrate excavation type is formed by excavating a surface of a semiconductor substrate 10. The flow channel 21 is formed between two opposite sides of the substrate 10, and ends thereof are open at side surfaces of the substrate 10. A top surface of the flow channel 21 is covered by a cap layer 15 of an insulating film. It should be noted that pillars 12 may be formed in the flow channel 21 for filtering and controlling surface tension.

A second microflow channel 22 is formed on the semiconductor substrate 10 to intersect with the flow channel 21. This flow channel 22 is a flow channel of an insulating film tunnel type whose top surface and side surfaces are surrounded by an insulating film 16, and ends thereof are open at side surfaces of the substrate 10. In addition, the semiconductor substrate 10 on which the second microflow channel 22 is formed is covered by a protective film 18, and the surface thereof is flattened. It should be noted that 21a in the figure denotes openings of the first microflow channel 21, and 22a denotes openings of the second microflow channel 22.

As shown in FIG. 5, four embankments (banks) 14 composed of a resin such as polyimide and epoxy are provided on a package board 60 to surround a region where the semiconductor microanalysis chip of FIG. 4 is mounted. That is, liquid receivers (reservoirs) 41 to 44 formed by the banks 14 are provided to be connected to the openings 21a and 22a of the respective flow channels 21 and 22 of the semiconductor microanalysis chip 1. Moreover, the banks 14 are provided to surround the respective reservoirs 41 to 44, and cutouts for connecting to the flow channel openings are provided at parts of the respective banks 14. In addition, the openings 21a of the flow channel 21 are connected to the reservoirs 41 and 43, and the openings 22a of the flow channel 22 are connected to the reservoirs 42 and 44. It should be noted that the package board 60 may be any board with a flat surface on which an electrical interconnect, etc., can be formed, and a glass board, a resin board, etc., can be used.

In addition, the electrodes 51 and 52 are formed in the two reservoirs 41 and 42, and are introduced to the outsides of the banks through spaces between the banks 14 and the package board 60. Furthermore, one of the electrodes 51 and 52 is connected to an IC 6 for current-voltage conversion, and the other is connected to an external electrical connection terminal (electrical signal input/output terminal) 7. It should be noted that the electrodes 51 and 52 need not necessarily be passed under the banks 14, and may be passed over the banks 14.

When the semiconductor microanalysis chip 1 having the structure shown in FIG. 4 is mounted on the package board 60 having the structure shown in FIG. 5, the openings 21a and 22a of the respective flow channels 21 and 22 of the chip 1 are connected to the respective reservoirs 41 to 44 as shown in FIG. 6. That is, the structure in which the flow channels 21 and 22 and the reservoirs 41 to 44 are connected while the semiconductor microanalysis chip 1 is mounted on the package board 60 can be obtained.

This structure is substantially the same as that of the semiconductor microanalysis chip shown FIG. 2. Accordingly, particles can be detected by dropping a sample liquid into the reservoirs 41 and 42 and monitoring a current between the electrodes 51 and 52. In addition, since the reservoirs 41 to 44 are provided on the package board 60 in this case, the reservoirs 41 to 44 need not be provided on the semiconductor substrate 10. Thus, the area of the semiconductor substrate 10 can be made smaller. Therefore, the semiconductor microanalysis chip 1 can be miniaturized, and the manufacturing cost thereof can be reduced.

It should be noted that the banks 14 may be formed by a method such as dispensing after the semiconductor microanalysis chip 1 is mounted on the package board 60 to provide the reservoirs 41 to 44. In this case, parts of the banks 14 can be brought into contact with the semiconductor microanalysis chip 1 without gap. Liquid leakage can thereby be prevented.

(Second Embodiment)

Figure 7:
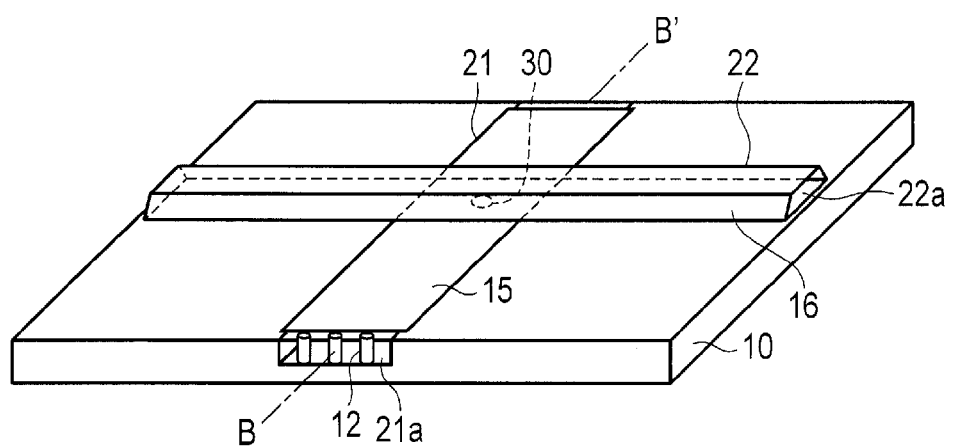
FIG. 7 is a perspective view showing a structure of a semiconductor microanalysis chip used in a microanalysis package according to a second embodiment.
Figure 8:
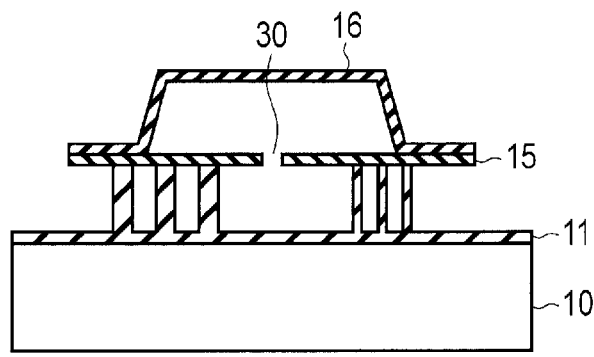
FIG. 8 is a cross-sectional view taken along line B-B' of FIG. 7.

FIG. 7 and FIG. 8 are illustrations for explaining a schematic structure of a microanalysis package according to a second embodiment. FIG. 7 is a perspective view, and FIG. 8 is a cross-sectional view taken along line B-B' of FIG. 7. It should be noted that the same portions as those of FIG. 4 to FIG. 6 are given the same numbers as those of FIG. 4 to FIG. 6, and detailed explanations thereof will be omitted.

The present embodiment differs from the above-described first embodiment in that a cap layer 15 which covers a top surface of a first microflow channel 21 is removed in the vicinity of ends of a chip.

If a liquid is introduced from a reservoir 41 formed on a package board 60 to the flow channel 21 of the chip 1, the liquid contacts an end of the flow channel 21 (entrance of the flow channel). At this time, if the entrance of the flow channel has a ceiling, surface tension at the entrance of the flow channel is large. Thus, there is a fear that the liquid may stop at the entrance of the flow channel and may not easily flow into the flow channel.

On the other hand, in the present embodiment, since parts of a ceiling portion of the flow channel 21 are offset inside, there is an advantage that a bottom surface at the ends of the flow channel is easily wet by a liquid, and further, a liquid easily flows into the flow channel because of capillarity at corners formed by the bottom surface and wall surfaces of the flow channel. Also regarding a flow channel 22, a cap layer 16 of a ceiling portion may be similarly removed in the vicinity of ends of the chip.

Therefore, according to the present embodiment, in addition to the advantages of the first embodiment, there is an advantage that a sample liquid can be more smoothly introduced into the flow channel 21 from the reservoir 41.

In addition, it is also possible to form parts (ends) of the upper flow channel 22 by excavating a semiconductor substrate 10 in the same way as the lower flow channel 21, and connect the ends and the center of the flow channel 22 by connection holes. In this case, openings 22a of the upper flow channel can be formed in the same shape as those of openings 21a of the lower flow channel 21.

(Modification)

It should be noted that the present invention is not limited to each of the above-described embodiments.

The structure of a semiconductor microanalysis chip is in no way limited to FIG. 4, FIG. 7, and FIG. 8, and it suffices that a detector such as a microaperture for detecting a particle, and a flow channel for injecting and ejecting a sample liquid for particle detection to the detector are provided.

Figure 9A:
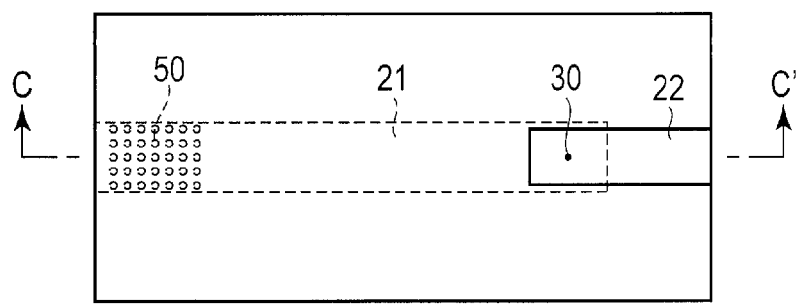
FIG. 9A is a plan view showing a modification of a semiconductor microanalysis chip used in the first and second embodiments.
Figure 9B:
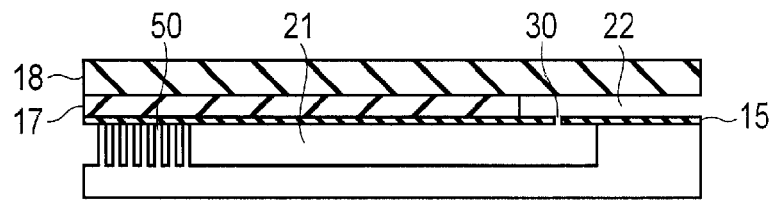
FIG. 9B is a cross-sectional view taken along line C-C' of FIG. 9A.

For example, flow channels which are open right and left may be provided as shown in the plan view of FIG. 9A and the cross-sectional view of FIG. 9B taken along line C-C' of FIG. 9A. In FIG. 9A and FIG. 9B, one end of a flow channel 21 of a substrate excavation type whose top surface is covered by an insulating film 15 is open on one side of a substrate 10, and an end of a flow channel 22 of an insulating film tunnel type whose top surface and side surfaces are surrounded by insulating films 17 and 18 is open on one side of the substrate 10. In addition, a microaperture 30 is formed in the insulating film 15 between the flow channels 21 and 22. Moreover, a column (pillar) array 50 extending from a bottom surface of the flow channel to a top surface of the flow channel is formed on an introduction opening side of the flow channel 21.

In addition, as shown in FIG. 10, first and second microflow channels 21 and 22 of a substrate excavation type may be provided with parts thereof close to each other, and electrodes 51 and 52 may be provided on both sides with a microaperture 30 interposed therebetween. It suffices that the electrodes 51 and 52 in this case are connected to interconnects on the package board 60 by bonding wires, etc., when the semiconductor microanalysis chip 1 is mounted on the package board 60.

In addition, as shown in FIG. 11, the first microflow channel 21 of a substrate excavation type and the second microflow channel 22 of an insulating film may be made to intersect with each other. This point is the same as in the first embodiment. Furthermore, the electrodes 51 and 52 are provided on both sides with the microaperture 30 interposed therebetween. Also in this case, it suffices that the electrodes 51 and 52 are connected to interconnects on the package board 60 by bonding wires, etc., when the semiconductor microanalysis chip 1 is mounted on the package board 60.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis package for detecting particles in a sample liquid, comprising:
    an analysis chip comprising a semiconductor substrate, the analysis chip comprising a flow channel in a top surface of the semiconductor substrate, the flow channel having two ends which are open at side surfaces of the semiconductor substrate, the side surfaces of the semiconductor substrate being adjacent to and intersecting the top surface of the semiconductor substrate, and the analysis chip comprising a microaperture which is provided in a middle of the flow channel and which allows a particle to pass therethrough;
    a package board on which the semiconductor substrate of the analysis chip is mounted, the package board differing in material from the semiconductor substrate;
    liquid receivers provided on the package board, the liquid receivers being connected to openings of the flow channel, respectively, and being surrounded by resin embankments provided to project from the package board; and
    electrodes, at least parts of which are provided on parts of bottom surfaces of the liquid receivers, the electrodes being provided at positions corresponding to an upstream side and a downstream side of the microaperture, respectively.

2. The analysis package of claim 1, further comprising an electrical signal input/output terminal provided on the package board, the electrical signal input/output terminal being electrically connected to the electrodes.

3. The analysis package of claim 1, wherein a ceiling of the flow channel is open at the ends of the flow channel.

4. The analysis package of claim 1, wherein the flow channel comprises first and second flow channels, parts of which contact each other, and the microaperture is formed at a contact portion between the first and second flow channels.

5. The analysis package of claim 4, wherein the first and second flow channels are flow channels of a substrate excavation type which are formed in parts of the top surface of the semiconductor substrate.

6. The analysis package of claim 1, wherein the package board is an insulating substrate.

7. An analysis package for detecting particles in a sample liquid, comprising:
    an analysis chip comprising a semiconductor substrate, the analysis chip comprising a first flow channel in a top surface of the semiconductor substrate, the flow channel having first and second ends, and a second flow channel provided above the first flow channel, the second flow channel having first and second ends, the first and second ends of the first flow channel and the first and second ends of the second flow channel being open at side surfaces of the analysis chip, the side surfaces of the analysis chip being adjacent to and intersecting the top surface of the semiconductor substrate, and the analysis chip comprising a microaperture which is provided at an overlap or intersection of the first and second flow channels and which allows a particle to pass therethrough;
    a package board on which the semiconductor substrate of the analysis chip is mounted, the package board differing in material from the semiconductor substrate;
    liquid receivers provided on the package board, the liquid receivers being connected to openings of the first and second flow channels, respectively; and
    electrodes, at least parts of which are provided on parts of bottom surfaces of the liquid receivers, the electrodes being provided at positions corresponding to an upstream side and a downstream side of the microaperture, respectively.

8. The analysis package of claim 7, wherein the first flow channel is a flow channel of a substrate excavation type which is formed in a part of the top surface of the semiconductor substrate, and the second flow channel is a flow channel of an insulating film tunnel type which is formed on the top surface of the semiconductor substrate and whose top surface and side surfaces are surrounded by an insulating film.

9. The analysis package of claim 1, further comprising a semiconductor device for detection mounted on the package board for converting a detection result of the analysis chip into an electrical signal.

10. The analysis package of claim 1, further comprising a pillar provided in the flow channel for filtering and controlling surface tension.

11. A package board comprising:
    a substrate comprising a region on which a semiconductor substrate of an analysis chip is mounted, the substrate of the package board differing in material from the semiconductor substrate of the analysis chip, and the analysis chip comprising a flow channel in a top surface of the semiconductor substrate, the flow channel having two ends which are open at side surfaces of the semiconductor substrate, the side surfaces of the semiconductor substrate being adjacent to and intersecting the top surface of the semiconductor substrate;
    liquid receivers provided on the substrate, the liquid receivers being connected to openings of the flow channel, respectively, and being surrounded by resin embankments provided to project from the substrate; and
    electrodes provided on parts of bottom surfaces of the liquid receivers.

12. The board of claim 11, further comprising an electrical signal input/output terminal provided on the substrate, the electrical signal input/output terminal being electrically connected to the electrodes.

13. The board of claim 11, further comprising a semiconductor device for detection provided on the substrate for converting a detection result of the analysis chip into an electrical signal.

14. The board of claim 11, wherein the substrate differing in material from the semiconductor substrate is an insulating substrate.

\* \* \* \* \*